United States Patent [19]

Haviv et al.

[11] 4,407,803

[45] Oct. 4, 1983

[54] ANTIINFLAMMATORY 1-(QUINOLINYL)-2-PYRAZOLINE DERIVATIVES

[75] Inventors: Fortuna Haviv, Dearfield; Robert W. Denet, Waukegan, both of Ill.

[73] Assignee: Abbott Laboratories, North Chicago, Ill.

[21] Appl. No.: 293,767

[22] Filed: Aug. 17, 1981

[51] Int. Cl.³ ............... A61K 31/47; C07D 401/04
[52] U.S. Cl. ........................ 424/258; 546/153; 546/155; 546/157; 546/159; 546/167; 546/171
[58] Field of Search ............ 424/258; 546/153, 155, 546/159, 157, 167, 171

[56] References Cited

U.S. PATENT DOCUMENTS

| 3,169,966 | 2/1965 | Schmidt et al. | 546/167 |
|---|---|---|---|
| 3,996,231 | 12/1976 | Wermouth et al. | 424/258 X |
| 4,226,773 | 10/1980 | Kynel | 424/273 P |

FOREIGN PATENT DOCUMENTS 484853  7/1952  Canada ..................... 546/167

OTHER PUBLICATIONS

Finar, et al., Chemical Abstracts, vol. 53, 7173d (1959).

*Primary Examiner*—Donald G. Daus
*Assistant Examiner*—Diana G. Rivers
*Attorney, Agent, or Firm*—Gildo E. Fato; Dennis K. Shelton

[57] ABSTRACT

Described are compounds of the formula wherein $R_2$–$R_8$ independently of one another denote hydrogen, loweralkyl, phenyl, alkoxy, halo, hydroxy, nitro, trifluoromethyl, with the proviso that at least one but no more than one of the substituents $R_2$–$R_8$ is and with the further provisos that at least four of the substituents $R_2$–$R_8$ are hydrogen and $R_2$ cannot be when $R_3$–$R_8$ are hydrogen, and pharmaceutically acceptable salts thereof.

The compounds are effective as antiinflammatory and antiasthma agents.

38 Claims, No Drawings

ANTIINFLAMMATORY 1-(QUINOLINYL)-2-PYRAZOLINE DERIVATIVES

BACKGROUND OF THE INVENTION

The present invention provides compositions for the treatment of rheumatoid arthritis, type III hypersensitivity diseases, diseases in which polymorphonuclear leukocyte accumulation contributes to the pathology, and other inflammatory conditions. An anti-inflammatory composition in dosage unit form is described.

SUMMARY OF THE INVENTION

The present invention is directed to compounds of the formula

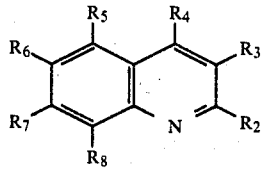

wherein $R_2$-$R_8$ independently of one another denote hydrogen, loweralkyl, phenyl, alkoxy, halo, hydroxy, nitro, trifluoromethyl,

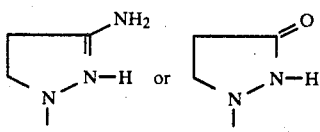

with the proviso that at least one but no more than one of the substituents $R_2$-$R_8$ is

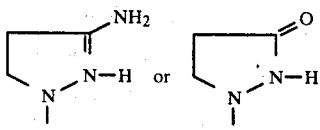

and with the further provisos that at least four of the substituents $R_2$-$R_8$ are hydrogen and $R_2$ cannot be

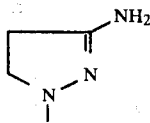

when $R_3$-$R_8$ are hydrogen, and pharmaceutically acceptable salts thereof.

The terms "loweralkyl" and "alkyl" as used herein refer to straight or branched chain alkyl radicals containing from 1 to 6 carbon atoms including but not limited to methyl, ethyl, n-propyl, iso-propyl, n-butyl, sec-butyl, 2-methylhexyl, n-pentyl, 1-methylbutyl, 2,2-dimethylbutyl, 2-methylpentyl, 2,2-dimethylpropyl, n-hexyl and the like.

The term "halo" as used herein refers to chloro, bromo, fluoro and iodo.

The compounds described in this invention are prepared by the reaction of the appropriate hydrazine quinolines with acrylonitrile in the presence of a base such as sodium methoxide, sodium ethoxide or sodium hydroxide, in a protic solvent such as a lower alcohol at a temperature of from about 50°–200° C. The reaction can also be carried out without any solvent at elevated temperatures of from about 50°–150° C. in the presence of an ammonium quatenary salt such as choline.

The term "pharmaceutically acceptable salts" includes nontoxic acid addition salts of the compounds of the invention which are generally prepared by reacting the free base with a suitable organic or inorganic acid. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, and like salts. Also included are metallic salts such as the sodium or potassium salt of the acid.

The present compounds may be administered to warm-blooded animals orally or parenterally. They can generally be administered with a pharmaceutical carrier. The term "pharmaceutical carrier," for the purpose of the present invention, is intended to refer to any medium that is suitable for the preparation of a dosage unit form, and thus includes the tablet medium or a pharmaceutically acceptable vehicle or solvent such as is ordinarily used in the preparation of intravenous or intramuscular solutions.

A pharmaceutical composition containing the compound can be administered to warm-blooded animals in parenteral or oral dosage form. For oral administration, amounts of from about 0.1 to 200 mg./kg. per day per patient are useful, with the total dose of up to 0.5 to 5.0 gm. per day being a suitable range for large animals, including humans.

For all dosage forms, the above exemplified compounds can be placed in capsules, formulated into pills, wafers or tablets in conventional fashion together with pharmaceutical carriers well known in the art. Tablets may be prepared for immediate release of the active compound or they may be made enteric, i.e., whereby the active ingredient is released slowly over a period of several hours from within the intestinal tract.

DETAILED DESCRIPTION OF THE INVENTION

In order to illustrate the manner in which the above compounds may be prepared and the properties of the compounds, reference is made to the following examples, which, however, are not meant to limit or restrict the scope of the invention in any respect.

EXAMPLE 1

1-(3'-Quinolinyl)-3-iminopyrazolidine

To a solution of sodium ethoxide, prepared by dissolving sodium (2.78 g.) in ethanol (150 ml.), was added under nitrogen and with stirring 3-hydrazinoquinoline hydrochloride (12.5 g.). Then dropwise was added acrylonitrile (3.3 g.). The mixture was refluxed overnight and then concentrated in vacuo to 30 ml. of volume. The product precipitated, filtered and crystallized from ethanol to give 1-(3'-quinolinyl)-3-iminopyrazolidine, m.p. 202°–204°.

EXAMPLE 2

When the following hydrazino quinolines were allowed to react with acrylonitrile as described in the procedure of Example 1, the following compounds were obtained:

| Hydrazines | Products |
|---|---|
| 2-hydrazinoquinoline | 1-(2'-quinolinyl)-3-imino-pyrazolidine; m.p. 208–210° C. |
| 4-hydrazino-7-chloroquinoline | 1-(7'-chloro-4'-quino-linyl)-3-imino pyrazolidine; m.p. 205–207° C. |
| 4-hydrazinoquinoline | 1-(4'-quinolinyl)-3-imino-pyrazolidine |
| 5-hydrazinoquinoline | 1-(5'-quinolinyl)-3-imino-pyrazolidine m.p. 240–243° C. |
| 6-hydrazinoquinoline | 1-(6'-quinolinyl)-3-imino-pyrazolidine |
| 7-hydrazinoquinoline | 1-(7'-quinolinyl)-3-imino-pyrazolidine |
| 8-hydrazinoquinoline | 1-(8'-quinolinyl)-3-imino-pyrazolidine, m.p. 184–186° C. |

EXAMPLE 3

1-(4'-Phenyl-2'-quinolinyl)-3-iminopyrazolidine

A stirred slurry of 2-amino-4-phenylquinoline (22 g.) in concentrated hydrochloric acid (50 ml.) was treated dropwise at 0° C. or below with sodium nitrite (7.0 g.) in cold water (35 ml.). The mixture was stirred for 0.5 hours at about 0° C. Stannous chloride dihydrate (56.7 g.) in cold concentrated hydrochloric acid (70 ml.) was added at 0° C. dropwise. The slurry was refrigerated overnight, filtered, and the precipitate was washed with saturated sodium chloride. The filtered solid was treated with excess concentrated sodium hydroxide solution and the hydrazine was extracted into ethyl acetate. The organic extract was washed, dried, decolorized and saturated with dry hydrogen chloride. On removal of the solvent, 2-hydrazino-4-phenylquinoline dihydrochloride was obtained. This compound was reacted with acrylonitrile using the same procedure described in Example 1.

EXAMPLE 4

When the following aminoquinolines are subjected to the same reaction conditions described in Example 3, the following compounds are obtained:

| Aminoquinolines | Products |
|---|---|
| 4,6-dimethyl-8-aminoquinoline | 1-(4',6'-dimethyl-8'-quinolinyl)-3-imino-pyrazolidine |
| 6-methoxy-8-aminoquinoline | 1-(6'-methoxy-8'-quinolinyl)-3-iminopyrazolidine |
| 6-bromo-8-aminoquinoline | 1-(6'-bromo-8'-quinolinyl)3-iminopyrazolidine |
| 3-amino-6-methylquinoline | 1-(6'-methyl-3'-quinolinyl)3-iminopyrazolidine |
| 3-amino-2-methylquinoline | 1-(2'-methyl-3'-quinolinyl)3-iminopyrazolidine |
| 3-amino-4-methyl-6-chloroquinoline | 1-(4'-methyl-6'-chloro-3'-quinolinyl)-3-iminopyrazolidine |
| 2-methyl-4-aminoquinoline | 1-(2'-methyl-4'-quinolinyl)-3-iminopyrazolidine |
| 2-amino-4-methylquinoline | 1-(4'-methyl-2'-quinolinyl)-3-iminopyrazolidine |
| 4-phenyl-6-methoxy-8-aminoquinoline | 1-(4'-phenyl-6'-meth-oxy-8'-quinolinyl)-3-iminopyrazolidine |
| 2-phenyl-4-hydroxy-6-aminoquinoline | 1-(2'-phenyl-4'-hydroxy-6'-quinolinyl)-3-iminopyrazolidine |
| 6-chloro-8-aminoquinoline | 1-(6'-chloro-8'-quinolinyl)-3-amino-pyrazolidine |
| 8-chloro-5-aminoquinoline | 1-(8'-chloro-5'-quinolinyl)-3-iminopyrazolidine |
| 7-chloro-6-aminoquinoline | 1-(7'-chloro-5'-quinolinyl)-3-iminopyrazolidine |

EXAMPLE 5

1-(7'-Trifluoromethyl-4'-quinolinyl)-3-iminopyrazolidine

A mixture of 4-chloro-7-trifluoromethylquinoline (21.95 g.) in ethanol (100 ml.) and hydrazine hydrate (60 g.) was refluxed overnight. The solvent and the excess of reagent were removed in vacuo to give 4-hydrazino-7-trifluoromethylquinoline hydrochloride.

The hydrazinoquinoline was reacted with acrylonitrile using the same conditions described in Example 1 to give 1-(7'-trifluoromethyl-4'-quinolyl)-3-iminopyrazolidine.

EXAMPLE 6

When the following chloroquinolines are subjected to the same reaction conditions described in Example 5, the following compounds are obtained:

| Chloroquinolines | Products |
|---|---|
| 2-chloro-6-methoxyquinoline | 1-(6'-methoxy-2'-quinolinyl)-3-iminopyrazolidine |
| 4-chloro-6-methylquinoline | 1-(6'-methyl-4'-quinolinyl)-3-iminopyrazolidine |
| 4-chloro-8-methoxyquinoline | 1-(8'-methoxy-4'-quinolinyl)-3-iminopyrazolidine |
| 4-chloro-8-methylquinoline | 1-(8'-methyl-4'-quinolinyl)-3-iminopyrazolidine |

EXAMPLE 7

1-(3'-Quinolinyl)-3-pyrazolidinone

A suspension of 1-(3'-quinolinyl)-3-iminopyrazolidine (3 g.) in concentrated sulfuric acid (5 ml.) and water (50 ml.) was refluxed for 5 hours. The mixture was basified with concentrated ammonium hydroxide at 0° C. The precipitate was washed with water to give 1-(3'-quinolinyl)-3-pyrazolidinone.

EXAMPLE 8

When the following quinolinyl iminopyrazolidines were subjected to the same reaction conditions described in Example 7, the following compounds were obtained:

| Quinolinyl-3-iminopyrazolidines | Products |
|---|---|
| 1-(2'-quinolinyl)-3-iminopyrazolidine | 1-(2'-quinolinyl)-3-pyrazolidinone |
| 1-(7-chloro-4'- | 1-(7'-chloro-4'-quinolinyl)- |

| Quinolinyl-3-iminopyrazolidines | Products |
|---|---|
| quinolinyl)-3-iminopyrazolidine | 3-pyrazolidinone |
| 1-(4'-quinolinyl)-3-iminopyrazolidine | 1-(4'-quinolinyl)-3-pyrazolidinone |
| 1-(5'-quinolinyl)-3-iminopyrazolidine | 1-(5'-quinolinyl)-3-pyrazolidinone |
| 1-(6'-quinolinyl-3-iminopyrazolidine | 1-(6'-quinolinyl)-3-pyrazolidinone |
| 1-(7'-quinolinyl)-3-iminopyrazolidine | 1-(7'-quinolinyl)-3-pyrazolidinone |
| 1-(8'-quinolinyl)-3-iminopyrazolidine | 1-(8'-quinolinyl)-3-pyrazolidinone |
| 1-(4'-phenyl-2'-quinolinyl)-3-iminopyrazolidine | 1-(4'-phenyl-2'-quinolinyl)-3-pyrazolidinone |
| 1-(4',6'-dimethyl-8'-quinolinyl)-3-iminopyrazolidine | 1-(4',6'-dimethyl-8'-quinolinyl)-3-pyrazolidinone |
| 1-(6'-methoxy-8'-quinolinyl)-3-iminopyrazolidine | 1-(6'-methoxy-8'-quinolinyl)-3-pyrazolidinone |
| 1-(6'-bromo-8'-quinolinyl)-3-iminopyrazolidine | 1-(6'-bromo-8'-quinolinyl)-3-pyrazolidinone |
| 1-(6'-methyl-3'-quinolinyl)-3-iminopyrazolidine | 1-(6'-methyl-3'-quinolinyl)-3-pyrazolidinone |
| 1-(4'-methyl-6'-chloro-3'-quinolinyl)-3-iminopyrazolidine | 1-(4'-methyl-6'-chloro-3'-quinolinyl)-3-pyrazolidinone |
| 1-(2'-methyl-4'-quinolinyl)-3-iminopyrazolidine | 1-(2'-methyl-4'-quinolinyl)-3-pyrazolidinone |
| 1-(4'-methyl-2'-quinolinyl)-3-iminopyrazolidine | 1-(4'-methyl-2'-quinolinyl)-3-pyrazolidinone |
| 1-(4'-phenyl-6'-methoxy-8'-quinolinyl)-3-iminopyrazolidine | 1-(4'-phenyl-6'-methoxy-8'-quinolinyl)-3-pyrazolidinone |
| 1-(2'-phenyl-4'-hydroxy-6'-quinolinyl)-3-iminopyrazolidine | 1-(2'-phenyl-4'-hydroxy-6'-quinolinyl)-3-pyrazolidinone |
| 1-(7'-trifluoromethyl-4'-quinolinyl)-3-iminopyrazolidine | 1-(7'-trifluoromethyl-4'-quinolinyl)-3-pyrazolidinone |

The compounds of the present invention have anti-inflammatory activity and inhibitory effect against Type III hypersensitivity reaction. These compounds are useful for the therapy of rheumatoid arthritis, other inflammatory conditions, Type III hypersensitivity diseases and in diseases in which polymorphonuclear leukocytes accumulation contributes to the pathology. The anti-inflammatory activity of these compounds was established by using a modification of the carrageenin pleurisy assay described by Vinegar et al. Proc. Soc. Exp. Biol. Med. 143:711 (1973). Table I shows the reduction in accumulation of exudate volume and leukocytes.

TABLE I

| Compound | Dose | % Inhibition Volume exudates | Cells |
|---|---|---|---|
| Phenylbutazone | 100 | 59 | 13 |
| 1-(3'-quinolinyl)-3-iminopyrazolidine | 60 | 86 | 71 |

The ability of these compounds to inhibit Type III hypersensitivity reactions was demonstrated using the reverse passive Arthus assay as described by Carter and Krause Fed. Proc. 35, 774 (1976). Each compound was administered orally to a group of four animals.

The Arthus reaction represents one of the oldest and best studied models of immunological injury. It is produced by the injection of antigen locally into a hyperimmunized animal or by the injection of a small amount of antibody into the skin of an animal that has just previously been given a large amount of soluble antigen intravenously. In both cases the antigen and antibody become deposited in the walls of small venules. Plasma complement is rapidly bound and activated. Within a few hours neutrophils (PMNs) accumulate resulting in disruption of the basement membrane of vessel walls and marked edema and hemorrage in the surrounding tissue.

Although the etiology of rheumatoid arthritis remains obscure, it is almost certain that immunological mechanisms play an important role in the pathogenesis of this disease. Therefore, inflammation induced by immunological reactions, which are believed to be important in the inflammatory processes of rheumatoid arthritis, make particularly desirable tools for the screening of potential anti-inflammatory agents. The usefulness of such a model depends upon how closely it represents the underlying pathological mechanisms of rheumatoid arthritis.

Based upon currently available evidence, a plausible sequence of events leading to the joint leisions in rheumatoid arthritis can be constructed. An initiating antigen, perhaps a transient synovial infection, results in an immune response and retention of the antigen within the joint structure. The interaction of antigen with developing antibodies results in the deposition of immune complexes. These complexes may fix and activate complement, causing the generation of a number of phlogistic and chemotactic substances. Phagocytosis of the complexes by attracted polymorphonuclear leukocytes (PMNs) leads to the release of lysosomal constituents. The enzymes released from lysosomes can erode articular cartilage and produce inflammation in the joint. The striking resemblance of these events to the Arthus phenomenon point to the utility of the Arthus reaction as a screen for anti-inflammatory compounds.

The reserve passive Arthus reaction test in rats is conducted as follows: Male Sprague-Dawley rats weighing approximately 130–160 g. are used, 4 rats per group. All animals are injected intravenously with 0.5 ml. 0.075% Bovine Serum Albumin (B.S.A.)+2% Evans Blue solution. Each rat then receives an oral dose of drug; one drug is administered per group.

Thirty minutes subsequent to drug dosing, each animal is injected intradermally with 0.05 ml. 1.44% Anti-B.S.A. into the dorsal skin. Four hours later the animals are sacrificed, the dorsal skin reflexed, and the lesion excised. Two perpendicular diameters of each lesion are measured. The average diameters of the lesions from the treated groups are compared with the average diameters from the control group to determine any drug effect.

Table II shows the percentage of reduction in lesion area produced by several representative compounds.

TABLE II

| Compound | Dose mg/kg | % Inhibition of lesion of dermal Arthus reaction |
|---|---|---|
| 1-(3'-quinolinyl)-3-iminopyrazolidine | 100 | 37 |
| 1-(2'-quinolinyl)-3-iminopyrazolidine | 100 | 72 |
| 1-(7'-chloro-4'-quinolinyl)-3- | 100 | 53 |

TABLE II-continued

| Compound | Dose mg/kg | % Inhibition of lesion of dermal Arthus reaction |
|---|---|---|
| iminopyrazolidine | | 5 |

What is claimed is:

1. A compound of the formula

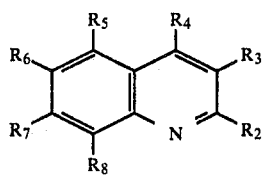

wherein $R_2$–$R_8$ independently of one another denote hydrogen, loweralkyl, phenyl, alkoxy, halo, hydroxy, nitro, trifluoromethyl,

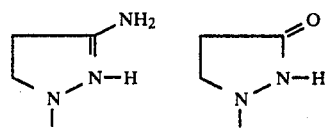

with the proviso that at least one but no more than one of the substituents $R_2$–$R_8$ is

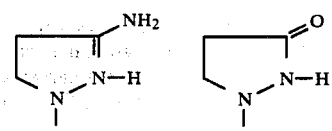

and with the further proviso that at least four of the substituents $R_2$–$R_8$ are hydrogen and, $R_2$ cannot be

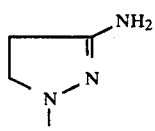

when $R_3$–$R_8$ are hydrogen, and pharmaceutically acceptable salts thereof.

2. A compound of the formula

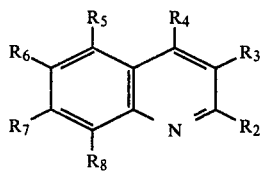

wherein $R_2$–$R_8$ independently of one another denote hydrogen, loweralkyl, phenyl, alkoxy, halo, hydroxy, nitro, trifluoromethyl, or

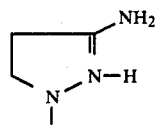

with the proviso that at least one but no more than one of the substituents $R_2$–$R_8$ is

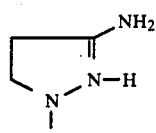

and with the further proviso that at least four of the substituents $R_2$–$R_8$ are hydrogen and, $R_2$ cannot be

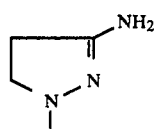

when $R_3$–$R_8$ are hydrogen, and pharmaceutically acceptable salts thereof.

3. A compound of the formula

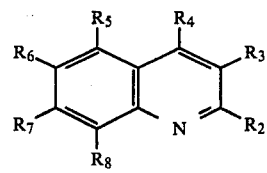

wherein $R_2$–$R_8$ independently of one another denote hydrogen, loweralkyl, phenyl, alkoxy, halo, hydroxy, nitro, trifluoromethyl, or

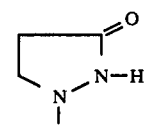

with the proviso that at least one but no more than one of the substituents $R_2$–$R_8$ is

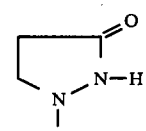

and with the further proviso that at least four of the substituents $R_2$–$R_8$ are hydrogen, and pharmaceutically acceptable salts thereof.

4. A compound of claim 2 wherein $R_2$ is hydrogen or loweralkyl, $R_3$ hydrogen or 3-amino-2-pyrazolinyl, $R_4$ is hydrogen or 3-amino-2-pyrazolinyl, $R_5$ is hydrogen, halo or 3-amino-2-pyrazolinyl, $R_6$ is hydrogen, halo or 3-amino-2-pyrazolinyl, $R_7$ is hydrogen, halo or 3-amino- 2-pyrazolinyl and $R_8$ is hydrogen, halo or 3-amino-2-pyrazolinyl.

5. A compound of claim 4 wherein $R_2$ is hydrogen or methyl, $R_5$ is hydrogen, chloro or 3-amino-2-pyrazolinyl, $R_6$ is hydrogen, chloro or 3-amino-2-pyrazolinyl, $R_7$ is hydrogen, chloro or 3-amino-2-pyrazolinyl and $R_8$ is hydrogen, chloro or 3-amino-2-pyrazolinyl.

6. A compound of claim 4 wherein $R_2$ is hydrogen, $R_3$ is hydrogen, $R_4$ is hydrogen, $R_5$ is hydrogen, halo or 3-amino-2-pyrazolinyl, $R_6$ is hydrogen, halo or 3-amino-2-pyrazolinyl, $R_7$ is hydrogen or halo, and $R_8$ is hydrogen, halo or 3-amino-2-pyrazolinyl.

7. A compound of claim 6 wherein $R_5$ is hydrogen, chloro or 3-amino-2-pyrazolinyl, $R_6$ is hydrogen, chloro or 3-amino-2-pyrazolinyl, $R_7$ is hydrogen or chloro, and $R_8$ is hydrogen, chloro or 3-amino-2-pyrazolinyl.

8. A compound of claim 4 wherein $R_2$ and $R_3$ are hydrogen, $R_4$ is 3-amino-2-pyrazolinyl, $R_5$ and $R_6$ are hydrogen, $R_7$ is chloro, and $R_8$ is hydrogen.

9. A compound of claim 4 wherein $R_2$, $R_3$ and $R_4$ are hydrogen, $R_5$ is 3-amino-2-pyrazolinyl, and $R_6$, $R_7$ and $R_8$ are hydrogen.

10. A compound of claim 4 wherein $R_2$ is hydrogen, $R_3$ is 3-amino-2-pyrazolinyl, and $R_4$, $R_5$, $R_6$, $R_7$ and $R_8$ are hydrogen.

11. A compound of claim 4 wherein $R_2$ is methyl, $R_3$ is hydrogen, $R_4$ is 3-amino-2-pyrazolinyl, and $R_5$, $R_6$ $R_7$ and $R_8$ are hydrogen.

12. A compound of claim 4 wherein $R_2$, $R_3$, $R_4$ and $R_5$ are hydrogen, $R_6$ is chloro, $R_7$ is hydrogen and $R_8$ is 3-amino-2-pyrazolinyl.

13. A compound of claim 4 wherein $R_2$, $R_3$, $R_4$, $R_5$, $R_6$ and $R_7$ are hydrogen and $R_8$ is 3-amino-2-pyrazolinyl.

14. A compound of claim 4 wherein $R_2$, $R_3$ and $R_4$ are hydrogen, $R_5$ is 3-amino-2-pyrazolinyl, $R_6$ and $R_7$ are hydrogen, and $R_8$ is chloro.

15. A compound of claim 4 wherein $R_2$, $R_3$, $R_4$, $R_5$, and $R_6$ are hydrogen, $R_7$ is 3-amino-2-pyrazolinyl, and $R_8$ is hydrogen.

16. A compound of claim 4 wherein $R_2$, $R_3$, $R_4$ and $R_5$ are hydrogen, $R_6$ is 3-amino-2-pyrazolinyl, $R_7$ is chloro and $R_8$ is hydrogen.

17. A compound of claim 4 wherein $R_2$, $R_3$, $R_4$ and $R_5$ are hydrogen, $R_6$ is 3-amino-2-pyrazolinyl, and $R_7$ and $R_8$ are hydrogen.

18. A compound of claim 4 wherein $R_2$, $R_3$ and $R_4$ are hydrogen, $R_5$ is chloro, $R_6$ is 3-amino-2-pyrazolinyl and $R_7$ and $R_8$ are hydrogen.

19. A compound of claim 3 wherein $R_2$, $R_3$, $R_4$ are hydrogen, $R_5$ is 3-keto-1-pyrazolidinyl, $R_6$ is hydrogen, $R_7$ is hydrogen and $R_8$ is hydrogen.

20. A compound of claim 3 wherein $R_2$, $R_3$, $R_4$ and $R_5$ are hydrogen, $R_6$ is 3-keto-1-pyrazolidinyl, and $R_7$ and $R_8$ are hydrogen.

21. A compound of claim 3 wherein $R_2$ is hydrogen, $R_3$ is 3-keto-1-pyrazolidinyl, and $R_4$, $R_5$, $R_6$, $R_7$ and $R_8$ are hydrogen.

22. A compound of claim 3 wherein $R_2$ is hydrogen, $R_3$ is hydrogen, $R_4$ is 3-keto-1-pyrazolidinyl, and $R_5$, $R_6$, $R_7$ and $R_8$ are hydrogen.

23. A method of treating or relieving the symptoms associated with inflammation comprising administering to a patient in need of such treatment a therapeutically effective amount of an antiinflammatory agent of the formula

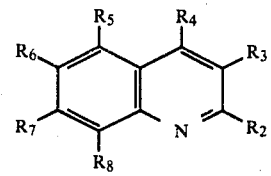

wherein $R_2$–$R_8$ independently of one another denote hydrogen, loweralkyl, phenyl, alkoxy, halo, hydroxy, nitro, trifluoromethyl,

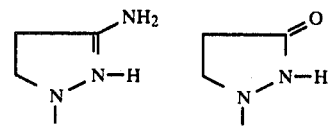

with the proviso that at least one but no more than one of the substituents $R_2$–$R_8$ is

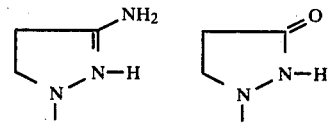

and with the further proviso that at least four of the substituents $R_2$–$R_8$ are hydrogen, and pharmaceutically acceptable salts thereof.

24. The method of claim 23 wherein $R_2$ is hydrogen or loweralkyl, $R_3$ is hydrogen or 3-amino-2-pyrazolinyl, $R_4$ is hydrogen or 3-amino-2-pyrazolinyl, $R_5$ is hydrogen, halo or 3-amino-2-pyrazolinyl, $R_6$ is hydrogen, halo or 3-amino-2-pyrazolinyl, $R_7$ is hydrogen, halo or 3-amino-2-pyrazolinyl and $R_8$ is hydrogen, halo or 3-amino-2-pyrazolinyl.

25. The method of claim 24 wherein $R_2$ is hydrogen or methyl, $R_5$ is hydrogen, chloro or 3-amino-2-pyrazolinyl, $R_6$ is hydrogen, chloro or 3-amino-2-pyrazolinyl, $R_7$ is hydrogen, chloro or 3-amino-2-pyrazolinyl and $R_8$ is hydrogen, chloro or 3-amino-2-pyrazolinyl.

26. The method of claim 23 wherein $R_2$ is hydrogen, $R_3$ is hydrogen, $R_4$ is hydrogen, $R_5$ is hydrogen, halo or 3-amino-2-pyrazolinyl, $R_6$ is hydrogen, halo or 3-amino-2-pyrazolinyl, $R_7$ is hydrogen or halo, and $R_8$ is hydrogen, halo or 3-amino-2-pyrazolinyl.

27. The method of claim 26 wherein $R_5$ is hydrogen, chloro or 3-amino-2-pyrazolinyl, $R_6$ is hydrogen, chloro or 3-amino-2-pyrazolinyl, $R_7$ is hydrogen or chloro and $R_8$ is hydrogen, chloro or 3-amino-2-pyrazolinyl.

28. The method of claim 23 wherein $R_2$, $R_3$, $R_4$, $R_5$, $R_6$ and $R_7$ are hydrogen and $R_8$ is 3-amino-2-pyrazolinyl.

29. The method of claim 23 wherein $R_2$, $R_3$ and $R_4$ are hydrogen, $R_5$ is 3-amino-2-pyrazolinyl, $R_6$ and $R_7$ are hydrogen, and $R_8$ is chloro.

30. The method of claim 23 wherein $R_2$, $R_3$, $R_4$, $R_5$ and $R_6$ are hydrogen, $R_7$ is 3-amino-2-pyrazolinyl, and $R_8$ is hydrogen.

31. The method of claim 23 wherein $R_2$, $R_3$, $R_4$ and $R_5$ are hydrogen, $R_6$ is 3-amino-2-pyrazolinyl, $R_7$ is chloro and $R_8$ is hydrogen.

32. The method of claim 23 wherein $R_2$, $R_3$, $R_4$ and $R_5$ are hydrogen, $R_6$ is 3-amino-2-pyrazolinyl and $R_7$ and $R_8$ are hydrogen.

33. The method of claim 23 wherein $R_2$, $R_3$ and $R_4$ are hydrogen, $R_5$ is chloro, $R_6$ is 3-amino-2-pyrazolinyl and $R_7$ and $R_8$ are hydrogen.

34. A pharmaceutical composition useful for the treatment of inflammatory conditions which comprises a compound of the formula

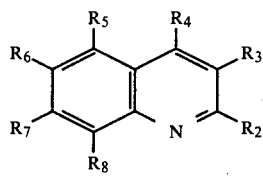

wherein $R_2$–$R_8$ independently of one another denote hydrogen, loweralkyl, phenyl, alkoxy, halo, hydroxy, nitro, trifluoromethyl,

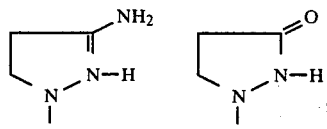

with the proviso that at least one but no more than one of the substituents $R_2$–$R_8$ is

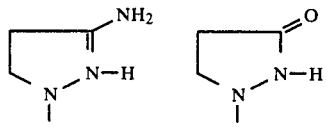

and with the further proviso that at least four of the substituents $R_2$–$R_8$ are hydrogen and pharmaceutically acceptable salts thereof, and a pharmaceutically acceptable carrier.

35. The composition of claim 34 wherein $R_2$ is hydrogen or loweralkyl, $R_3$ is hydrogen or 3-amino-2-pyrazolinyl, $R_4$ is hydrogen or 3-amino-2-pyrazolinyl, $R_5$ is hydrogen, halo or 3-amino-2-pyrazolinyl, $R_6$ is hydrogen, halo or 3-amino-pyrazolinyl, $R_7$ is hydrogen, halo or 3-amino-2-pyrazolinyl and $R_8$ is hydrogen, halo or 3-amino-2-pyrazolinyl.

36. The composition fo claim 35 wherein $R_2$ is hydrogen, or methyl, $R_5$ is hydrogen, chloro or 3-amino-2-pyrazolinyl, $R_6$ is hydrogen, chloro or 3-amino-2-pyrazolinyl, $R_7$ is hydrogen, chloro or 3-amino-2-pyrazolinyl and $R_8$ is hydrogen, chloro or 3-amino-2-pyrazolinyl.

37. The composition of claim 34 wherein $R_2$ is hydrogen, $R_3$ is hydrogen, $R_4$ is hydrogen, $R_5$ is hydrogen, halo or 3-amino-2-pyrazolinyl, $R_6$ is hydrogen, halo or 3-amino-2-pyrazolinyl, $R_7$ is hydrogen or halo and $R_8$ is hydrogen, halo or 3-amino-2-pyrazolinyl.

38. The composition of claim 37 wherein $R_2$ is hydrogen, chloro or 3-amino-2-pyrazolinyl, $R_6$ is hydrogen, chloro or 3-amino-2-pyrazolinyl, $R_7$ is hydrogen or chloro and $R_8$ is hydrogen, chloro or 3-amino-2-pyrazolinyl.

* * * * *